(12) United States Patent
Lockemeyer

(10) Patent No.: US 6,368,998 B1
(45) Date of Patent: Apr. 9, 2002

(54) PROCESS FOR PREPARING CATALYST WITH IMPROVED CATALYTIC PROPERTIES

(75) Inventor: John Robert Lockemeyer, Sugar Land, TX (US)

(73) Assignee: Shell Oil Company, Houston, TX (US)

( * ) Notice: Subject to any disclaimer, the term of this patent is extended or adjusted under 35 U.S.C. 154(b) by 0 days.

(21) Appl. No.: 09/392,523

(22) Filed: Sep. 9, 1999

Related U.S. Application Data

(60) Provisional application No. 60/100,194, filed on Sep. 14, 1998.

(51) Int. Cl.⁷ .............................. B01J 23/50; B01J 32/00
(52) U.S. Cl. ........................................ 502/347; 502/300
(58) Field of Search ................................ 502/344, 347, 502/300

(56) References Cited

U.S. PATENT DOCUMENTS

| | | | |
|---|---|---|---|
| 2,424,083 A * | 7/1947 | Finch et al. | |
| 2,901,441 A | 8/1959 | Waterman | 252/463 |
| 3,972,829 A | 8/1976 | Michalko | 252/430 |
| 4,005,049 A | 1/1977 | Fields | 252/467 |
| 4,125,480 A | 11/1978 | Maxwell | 252/414 |
| 4,186,106 A | 1/1980 | Rebsdat et al. | 252/414 |
| 4,212,772 A | 7/1980 | Mross et al. | 252/476 |
| 4,356,312 A * | 10/1982 | Nielsen et al. | |
| 4,361,500 A | 11/1982 | Mathe et al. | 252/430 |
| 4,361,504 A * | 11/1982 | Solomon et al. | |
| 4,366,092 A | 12/1982 | Winterton | 252/476 |
| 4,367,167 A | 1/1983 | Lee et al. | 252/472 |
| 4,379,134 A * | 4/1983 | Weber et al. | |
| 4,382,149 A * | 5/1983 | Krueger | |
| 4,532,231 A * | 7/1985 | Johnson | |
| 4,628,129 A * | 12/1986 | Bartley | |
| 4,797,270 A | 1/1989 | Cendan et al. | 423/625 |
| 4,797,279 A | 1/1989 | Karamata et al. | 424/93 |
| 4,810,689 A | 3/1989 | Hayden | 502/347 |
| 4,874,739 A | 10/1989 | Boxhoorn | 502/218 |
| 4,886,917 A | 12/1989 | Knopf et al. | 568/623 |
| 4,908,343 A | 3/1990 | Bhasin | 502/218 |
| 4,916,243 A | 4/1990 | Bhasin et al. | 549/534 |
| 4,994,587 A * | 2/1991 | Notermann et al. | |
| 4,994,588 A | 2/1991 | Kapicak et al. | 549/534 |
| 4,994,589 A | 2/1991 | Notermann | 549/534 |
| 5,037,794 A | 8/1991 | Magistro | 502/355 |
| 5,055,442 A | 10/1991 | Osaka et al. | 502/439 |
| 5,057,481 A | 10/1991 | Bhasin | 502/208 |
| 5,100,859 A | 3/1992 | Gerdes et al. | 502/439 |
| 5,112,795 A | 5/1992 | Minahan et al. | 502/324 |
| 5,187,140 A * | 2/1993 | Thorsteinson et al. | |
| 5,364,826 A | 11/1994 | Kemp | 502/315 |
| 5,374,748 A | 12/1994 | Rizkalla | 549/534 |
| 5,380,697 A | 1/1995 | Matusz et al. | 502/348 |
| 5,380,885 A | 1/1995 | Kemp | 549/536 |
| 5,387,751 A | 2/1995 | Hayden et al. | 549/534 |
| 5,418,202 A | 5/1995 | Evans et al. | 502/348 |
| 5,447,897 A | 9/1995 | Kemp | 502/303 |
| 5,486,628 A | 1/1996 | Kemp | 549/536 |
| 5,545,603 A | 8/1996 | Kemp | 502/347 |
| 5,597,773 A | 1/1997 | Evans et al. | 502/348 |
| 5,663,385 A | 9/1997 | Kemp | 549/536 |
| 5,668,077 A | 9/1997 | Klopries et al. | 502/347 |
| 5,703,253 A | 12/1997 | Evans et al. | 549/536 |
| 5,734,068 A | 3/1998 | Klopries et al. | 549/536 |
| 5,739,075 A * | 4/1998 | Matusz | |
| 6,103,916 A * | 8/2000 | Takada et al. | |

FOREIGN PATENT DOCUMENTS

| | | |
|---|---|---|
| EP | 211521 | 2/1987 |
| EP | 563 414 A1 | 10/1993 |
| EP | 0937498 A1 | 8/1999 |
| FR | 2.005.978 | 10/1969 |
| GB | 568 978 | 1/1946 |
| JP | 56105750 | 8/1981 |
| JP | 56164013 | 12/1981 |
| WO | 96/23585 | 8/1996 |
| WO | 96/41848 | 12/1996 |

* cited by examiner

*Primary Examiner*—Steven P. Griffin
*Assistant Examiner*—Christina Idebrando
(74) *Attorney, Agent, or Firm*—Beverlee G. Steinberg

(57) ABSTRACT

This invention relates to a process for the preparation of a catalyst having improved properties, the process comprising selecting a carrier, lowering the concentration of ionizable species present on the surface of the carrier, and depositing a catalytically effective amount of one or more catalytically reactive metals on the carrier. The invention further relates to catalyst made from the process.

39 Claims, No Drawings

PROCESS FOR PREPARING CATALYST WITH IMPROVED CATALYTIC PROPERTIES

This application claims the priority of Provisional No. 60/100,194, filed Sep. 14, 1998.

FIELD OF THE INVENTION

The invention relates to a process for the preparation of catalyst with improved catalytic properties, particularly improved initial activity, initial selectivity and/or activity performance over time and/or selectivity performance over time.

BACKGROUND OF THE INVENTION

The presence of certain species contained in the carriers of catalysts can be detrimental to the metal deposition process and/or catalyst performance and it is commonly believed that the concentration of these detrimental species must be controlled throughout the bulk of carrier. One way of controlling the amount of impurities through the bulk, although expensive, is by the use of purer raw materials. For example, U.S. Pat. No. 4,797,270 discloses water washing to reduce the sodium content of an alumina powder. The pH of the wash water may need to be adjusted for extraction of other metals and Japanese patent JP56164013 discloses the use of a low pH (acid) to extract uranium and thorium from a calcined α-alumina raw material.

Several procedures in the art teach that washing after deposition of the catalytic metal is helpful. U.S. Pat. Nos. 4,361,504 and 4,366,092 suggest that ethylene oxide catalyst be water washed after the deposition of silver or silver/gold on the carrier. EP-211521 discloses washing of a catalyst with hot water to remove basic materials left on the catalyst from a silver impregnation process or the physical deposition of alkali metals. U.S. Pat. No. 4,367,167 discloses a process for preparing a supported catalyst wherein an impregnated support is immersed in an inert water immiscible organic solvent containing a dissolved aliphatic amine. U.S. Pat. No. 4,810,689 discloses depositing a silver compound, decomposing the silver compound to silver in the presence of an alkali metal compound, removing organic deposits by washing and introducing fresh alkali metal by impregnation during or after the washing stage. U.S. Pat. Nos. 4,186,106 and 4,125,480 disclose washing with an inert liquid after deposition of the catalytic metal and before deposition of a promoter material.

U.S. Pat. No. 4,908,343 teaches that it may be desirable to remove cations which are exchangeable with the alkali and alkaline earth metals contained in the impregnating solution, to allow for ease of repeatability in the use and reuse of the impregnating solution. No methods are taught for such removal; however, it is commonly known in the art that acids are highly effective cation removal solutions. U.S. Pat. No. 2,901,441 teaches washing a carrier with lactic acid then flushing with water.

The prior art remains concerned with the total amount of impurities; i.e., impurities throughout the bulk. Unfortunately, the impurity removal techniques taught typically attack the carrier itself. It has surprisingly been found that the metal deposition and/or catalytic properties of a catalyst may be greatly improved by controlling the purity of the surface of the carrier rather than the purity of the carrier bulk, such that the total amount of impurities may actually be high as long as the surface amount of impurities are maintained at a low level.

SUMMARY OF THE INVENTION

According to one embodiment of the invention, there is provided a process for improving the properties of a carrier, said process comprising selecting a carrier; and lowering a concentration of one or more ionizable species present on a surface of said carrier.

There is further provided a process for improving a carrier comprising selecting one or more materials; lowering a concentration of one or more ionizable species present in at least one of said one or more materials; forming a carrier comprising said one or more materials; and lowering a concentration of one or more ionizable species present on a surface of said carrier.

There is still further provided a process for improving the catalytic properties of a catalyst, said process comprising:

selecting a carrier;

lowering a concentration of one or more ionizable species on a surface of said carrier by a means effective in solubilizing the ionizable species and removing that species, or rendering the ionizable species insoluble, or rendering the ionizable species immobile;

optionally drying said carrier;

depositing a catalytically effective amount of one or more catalytically reactive metals on said carrier, thereby forming a catalyst precursor; and optionally drying said catalyst precursor.

In another embodiment of the invention, there is provided a process for improving the catalytic properties of a catalyst, said process comprising:

selecting one or more materials;

lowering a concentration of one or more ionizable species present in at least one of said one or more materials by a means effective in solubilizing ionizable species and removing that species, or rendering the ionizable species insoluble, or rendering the ionizable species immobile;

forming a carrier comprising said one or more materials;

optionally lowering a concentration of one or more ionizable species on a surface of said carrier by a means effective in solubilizing and removing said ionizable species or rendering said ionizable species insoluble;

optionally drying said carrier;

depositing a catalytically effective amount of one or more catalytically reactive metals on said carrier, thereby forming a catalyst precursor; and optionally drying said catalyst precursor.

In yet another embodiment of the invention there is provided a process for preparing a catalyst suitable for the vapor phase production of epoxides, said process comprising:

selecting a carrier;

lowering a concentration of one or more ionizable species present on a surface of said carrier;

optionally drying said carrier; and depositing a catalytically effective amount of one or more catalytically reactive metals on said carrier.

The invention also provides for catalyst made by the processes of the embodiments herein described.

DESCRIPTION OF THE PREFERRED EMBODIMENTS

It has been found that carriers which have been treated to reduce certain undesirable ionizable species, particularly anionic species, which are present on the surface of the carrier provide catalysts with improved catalytic properties, such as activity, selectivity and activity and/or selectivity performance over time, when compared with the performance of catalysts made from carriers which have not been so treated. The process is believed to work to improve the properties of most catalysts, no matter how impure the bulk carrier material, compared to a catalyst made with an untreated carrier. Further, the process will work for organic or inorganic carriers.

The process is effective in improving one or more of the catalytic properties of a catalyst wherein a catalytically reactive metal is deposited or impregnated upon a carrier which contains ionizable species on its surface. "Improvement in catalytic properties" as used herein means the properties of the catalyst are improved as compared to a catalyst made from the same carrier which has not been treated to lower surface ionizable species. Catalytic properties include catalyst activity, selectivity, activity and/or selectivity performance over time, operability (resistance to runaway), conversion and work rate.

The process requires that the concentration of undesirable ionizable species present on the surface of the carrier be reduced. As used herein, the "surface" of the carrier is that area of the carrier which may be measured by the standard method of Brunauer, Emmett and Teller (BET). Specifically, the surface of the carrier is the site at which reaction takes place. An "ionizable" species is a species which is capable of being rendered ionic, where the term "ionic" or "ion" refers to an electrically charged chemical moiety.

Carriers are commonly inorganic materials such as, for example, alumina-, silica-, or titania-based compounds, or combinations thereof, such as alumina-silica carriers. Carriers may also be made from carbon-based materials such as, for example, charcoal, activated carbon, or fullerenes. Ionizable species typically present on the inorganic type carriers include sodium, potassium, aluminates, soluble silicate, calcium, magnesium, aluminosilicate, cesium, lithium, and combinations thereof. Of particular concern are the ionizable anionic species present on the surface, particularly ionizable silicates. Lowering the undesirable ionizable species concentration may be accomplished by any means (i) which is effective in rendering the ionizable species ionic and removing that species, or (ii) which renders the ionizable species insoluble, or (iii) which renders the ionizable species immobile; however, use of aggressive media is discouraged as these media tend to dissolve the carrier, extract too much material from the bulk, and generate acidic or basic sites in the pores. Acids, besides being an aggressive medium, will remove the cations on a carrier but are fairly ineffectual in removing the undesirable anions, such as silicates. Effective means of lowering concentration include washing the carrier; ion exchange; volatilizing, precipitating, or sequestering the impurities; causing a reaction to make the ionizable species on the surface insoluble; and combinations thereof. Examples of wash and ion exchange solutions include aqueous and/or organic solvent-based solutions which may also contain tetraethylammonium hydroxide, ammonium acetate, lithium carbonate, barium acetate, strontium acetate, crown ether, methanol, ethanol, dimethylformamide, and mixtures thereof. The formed carrier may be treated, or the materials used to form the carrier may be treated before the carrier is manufactured. When the carrier materials are treated before the carrier is formed, still further improvement may be seen by also treating the surface of the formed carrier. The carrier may be dried following the ionizable species reduction treatment.

To make a catalyst from the carrier, the carrier is typically impregnated with metal compound(s), complex(es) and/or salt(s) dissolved in a suitable solvent sufficient to deposit or impregnate a catalytically effective amount of metal on the carrier. As used herein, "catalytically effective amount" means an amount of metal that provides a measurable catalytic effect. For example, a catalytically effective amount of metal when referring to an olefin epoxidation catalyst is that amount of metal which provides a measurable conversion of olefin and oxygen to alkylene oxide.

Further improvement in the catalyst properties are seen when the metal deposition is effected by contacting the carrier with an impregnation solution whose hydrogen ion activity has been lowered. "Hydrogen ion activity" as used herein is the hydrogen ion activity as measured by the potential of a hydrogen ion selective electrode. As used herein, a solution with "lowered" hydrogen ion activity refers to a solution whose hydrogen activity has been altered by the addition of a base, such that the hydrogen ion activity of the altered solution is lowered compared to the hydrogen ion activity of the same solution in an unaltered state. The base selected to alter the solution may be chosen from any base or compound with a pKb lower than the original impregnation solution. It is particularly desirable to chose a base which does not alter the formulation of the impregnation solution; i.e., which does not alter the desired metals concentration in the impregnation solution and deposited on the carrier. Organic bases will not alter the impregnation solution metals concentrations, examples of which are tetraalkylammonium hydroxides and 1,8-bis-(dimethylamino)-naphthalene. If changing the metals concentration of the impregnation solution is not a concern, metal hydroxides may be used.

When the impregnation solution is at least partially aqueous, an indication of the change in the hydrogen activity may be measured with a pH meter, with the understanding that the measurement obtained is not pH by a true, aqueous definition. "'Measured pH'" as used herein shall mean such a non-aqueous system pH measurement using a standard pH probe. Even small changes in the "measured pH" from the initial impregnation solution to that with added base are effective and improvements in catalytic properties continue as the "measured pH" change increases with base addition. High base additions do not seem to adversely affect catalyst performance; however, high additions of hydroxides have been seen to cause sludging of the impregnation solution, creating manufacturing difficulties. When the base addition is too low, the hydrogen ion activity will not be affected. The hydrogen ion activity lowering procedure is also quite effective when used by itself; i.e., when no ionizable species concentrations are lowered prior to impregnation.

The impregnated carrier, also known as a catalyst precursor, may be dried in the presence of an atmosphere which also reduces the catalytic metal. Drying methods known in the art include steam drying, drying in an atmosphere with a controlled oxygen concentration, drying in a reducing atmosphere, air drying, and staged drying using a suitable ramped or staged temperature curve.

By way of example, the process will be described in more detail for a catalyst suitable for the vapor phase production of epoxides, also known as an epoxidation catalyst.

First, a carrier is selected, in the case of an epoxidation catalyst the carrier is typically an inorganic material, such as for example, an alumina-based carrier such as α-alumina. The concentration of undesirable ionizable species present on the surface of the carrier are reduced to create a "cleansed" carrier. Or, alternatively, the concentration of ionizable species in the materials used to make the carrier may be reduced prior to formation of the carrier. If the carrier raw materials are treated, the formed carrier may be retreated for further improvement.

Ionizable species present on an α-alumina carrier, for example, typically include sodium, potassium, aluminates, soluble silicates, calcium, magnesium, aluminosilicates, and combinations thereof. It has been found that silicates, and certain other anions, are particularly undesirable ionizable species in an epoxidation catalyst. The solubilization rate of silicates may be measured by inductively coupled plasma (ICP) techniques and the amount of silicon species on a surface may be measured by x-ray photoelectron spectroscopy (XPS); however, since sodium is soluble in the same solutions that silicates are soluble in, the solubilization rate of sodium becomes a simpler check of the ionic species removal. Another measurement technique is to measure the change in electrical conductivity of the treatment solution.

The concentration of the undesirable ionizable species may lowered by any means which is effective in rendering the ionizable species ionic and removing that species, or rendering the ionizable species insoluble, or rendering the ionizable species immobile. Means effective in lowering the concentration of the undesirable ionizable species on the surface include washing, ion exchange, volatilization, precipitation, sequestration, impurity control and combinations thereof. Cleansing of an alumina-based carrier may be efficiently and cost-effectively accomplished by washing or ion exchange. Any solution capable of reducing the concentration of the undesirable ionizable species present, particularly the anionic ionizable species, and most particularly ionizable silicates, may be used.

After the concentration of the surface ionizable species are lowered, the carrier is optionally dried. When aqueous or organic solvent washing is used, drying or some similar method is recommended to displace the wash solution from the carrier pores. The carrier is now ready for a catalytically reactive metal to be deposited or impregnated thereon. For further improvement in catalytic properties, the hydrogen ion activity of the impregnation solution is optionally lowered, such as by the addition of a base. The typical impregnation solution for an epoxidation catalyst begins quite basic, so a strong base is used to further lower the hydrogen ion activity. Examples of strong bases include alkyl ammonium hydroxide such as tetraethylammonium hydroxide, and metal hydroxide such as lithium hydroxide and cesium hydroxide. In order to maintain the desired impregnation solution formulation and metal loading, a organic base such as tetraethylammonium hydroxide is preferred. Base additions in these systems typically result in a "measured pH" change ranging up to about 3 pH units, realizing that the "measured pH" is not a true pH since the impregnation system is not aqueous.

If an excess of impregnation solution is used, the impregnated carrier is subsequently separated from the solution before the deposited metal compound is reduced. Promoters, components which work effectively to provide an improvement in one or more of the catalytic properties of the catalyst when compared to a catalyst not containing such components, may also be deposited on the carrier either prior to, coincidentally with, or subsequent to the deposition of the catalytically reactive metal.

The resulting epoxidation catalysts just described are used for the vapor phase production of epoxides. A typical epoxidation process involves loading catalysts into a reactor. The feedstock to be converted, typically a mixture of ethylene, oxygen, carbon dioxide, nitrogen and ethyl chloride, is passed over the catalyst bed at pressure and temperature. The catalyst converts the feedstock to an outlet stream product which contains ethylene oxide. Nitrogen oxides ($No_x$) may also be added to the feedstock to boost catalyst conversion performance.

Other embodiments of the invention provide catalysts made by the processes just described.

Having generally described the invention, a further understanding may be obtained by reference to the following examples, which are provided for purposes of illustration only and are not intended to be limiting unless otherwise specified.

EXAMPLES

Carriers

The properties of the carriers used in the Examples are given in Table I.

TABLE I

| Carrier | A | B | C | D | E |
|---|---|---|---|---|---|
| B.E.T. Surface Area ($m^2/g$) [a] | 0.84 | 0.97 | 0.78 | 0.76 | 0.87 |
| Water Absorption (%) | 39.7 | 46.2 | 37.6 | 32.5 | 43.4 |
| Crush Strength (kg) [b] | 6.53 | 8.07 | 12.29 | 10.93 | 5.44 |
| Total Pore Volume (cc/g) [c] | 0.408 | 0.460 | 0.390 | 0.430 | |
| Median Pore Diameter (microns) [c] | 1.8 | 2.7 | 1.3 | 4.6 | |
| $SiO_2$ (% w) | 0.5 | 0.8 | 0.1 | 0.5 | 0.5 |
| Bulk Acid-Leachable Na (ppmw) | 438 | 752 | 186 | 1907 | 339 |
| Bulk Acid-Leachable K (ppmw) | 85 | 438 | 109 | 71 | 37 |
| Bulk Acid-Leachable Ca (ppmw) | 207 | 508 | 526 | 293 | 123 |
| Bulk Acid-Leachable Al (ppmw) | 744 | 1553 | 657 | 1978 | 499 |
| Bulk Acid-Leachable $SiO_2$ (ppmw) | 808 | 1879 | 4560 | >2000 | 600 |
| alpha-Alumina (% w) | Bal | Bal | Bal | Bal | Bal |

[a] Method of Brunauer, Emmett and Teller, loc. cit.
[b] Flat Plate Crush Strength, single pellet.
[c] Determined by mercury intrusion to $3.8 \times 10^8$ Pa using Micromeritics Autopore 9200 or 9210 (130° contact angle, 0.473 N/m surface tension of Hg).

Carrier Water Washing Procedures for Examples 1, 2, 3, 4, 5, 7, 8, 8b, 10, 12

Carrier washing was carried out by immersing 100 grams of carrier in 300 grams of boiling de-ionized water for 15 minutes. The carrier was then removed and placed in a fresh 300 grams of boiling water for another 15 minutes. This procedure was repeated once more for a total of three immersions, at which point the carrier was separated from the water and dried in a well ventilated oven at 150° C. for 18 hours. The dried carrier was then used for preparation of a catalyst by the procedures outlined in the following Examples.

Impregnation Solution

A silver-amine-oxalate stock solution was prepared by the following procedure:

415 g of reagent-grade sodium hydroxide were dissolved in 2340 ml de-ionized water and the temperature was adjusted to 50° C.

1699 g high purity "Spectropure" silver nitrate were dissolved in 2100 ml de-ionized water and the temperature was adjusted to 50° C.

The sodium hydroxide solution was added slowly to the silver nitrate solution, with stirring, while maintaining a solution temperature of 50° C. The mixture was stirred for 15 minutes, then the temperature was lowered to 40° C.

Water was removed from the precipitate created in the mixing step and the conductivity of the water, which contained sodium and nitrate ions, was measured. An amount of fresh deionized water equal to the amount removed was added back to the silver solution. The solution was stirred for 15 minutes at 40° C. The process was repeated until the conductivity of the water removed was less than 90 μmho/cm. 1500 ml fresh deionized water was then added.

630 g of high-purity oxalic acid dihydrate were added in approximately 100 g increments. The temperature was keep at 40° C. and the pH was kept above 7.8.

Water was removed from the mixture to leave a highly concentrated silver-containing slurry. The silver oxalate slurry was cooled to 30° C.

699 g of 92% w ethylenediamine (8% de-ionized water) was added while maintaining a temperature no greater than 30° C. The resulting solution contained approximately 27–33% w silver.

Enough 45% w aqueous CsOH and water was added to this solution to give a finished catalyst having 14.5% w silver and a desired cesium loading (see Examples).

Sodium and Silicate Measurement Procedures

The sodium solubilization rate of selected carriers was determined by measuring the sodium content of the extracting medium with an Orion model no. 8611BN sodium selective electrode connected to an Orion model 290A voltmeter, and by XPS. The silicate solubilization rates were measured by XPS. In a typical experiment, 300 grams of carrier was boiled in 900 grams of de-ionized water for a total of fifteen minutes. During this period, 3 ml aliquots were taken at predetermined intervals. The sodium content of each aliquot was analyzed at 25° C. using procedures well established for ion selective electrodes. The sodium concentration in the solution sampled at 5 minutes is used to evaluate the carrier as being a good or poor candidate for catalyst preparation. Results are given in Table II.

The XPS analyses were performed in a VG ESCALAB mkII X-ray photoelectron spectrometer. Non-monochromatized Al kα (1484.6 eV) X-rays were used as the excitation source. The electron kinetic energy analyzer was a 150 degree spherical sector analyzer equipped with a three channeltron detection system. All spectra were obtained in the constant analyzer pass energy mode with the pass energy set at 50 eV. Prior to analysis, samples were lightly crushed with a mortar and pestle and mounted onto a sample stub using double-sided tape. The analysis region was roughly 3 mm×5 mm. The Al2s peak was used for charge correction and was corrected to 118.5 eV. Linear baselines were used for measuring the peak heights of the Al2s, Si2s, and Na1s lines, and a horizontal baseline starting at a bonding energy of 105.5 eV was used for measuring the height of the Si2p line due to an interference with an aluminum Auger line. Peak intensities were converted to relative molar values using the following empirically derived sensitivity factors:

Al2s 0.22, Si2p 0.32, Si2s 0.24 and Na1s 1.72 and the following relationship:

$$\text{Relative number of atoms} = \frac{(\text{peak intensity/sensitivity factor}) * 100}{(\text{Al2s intensity}/0.22)}$$

The results of the XPS measurements are given in Table III. The numbers reported for XPS measurements are the number of atoms detected relative to 100 aluminum atoms. The XPS silicon values reported are the average of the Si2p and Si2s values.

TABLE II

Sodium Solubilization Rates for Selected α-Alumina Carriers

| Carrier | Bulk Na Unwashed Carrier (ppmw)[a] | Extracted Na Unwashed Carrier (ppmw) | Extracted Na Washed Carrier (ppmw) |
|---|---|---|---|
| A | 438 | 9.2 | 1.3 |
| A[b] | 438 | 9.2 | 1.2 |
| B | 752 | 9.2 | 1.8 |
| C | 186 | 10.2 | — |

[a] From Table I.
[b] Following ammonium acetate exchange as described in Example 9.

TABLE III

Na and Si XPS for Selected α-Alumina Carriers

| Carrier | XPS Na Unwashed Carrier (atom %) | XPS Na Washed Carrier (atom %) | Change in Na Unwashed to Washed (%) | XPS Si Unwashed Carrier (atom %) | XPS Si Washed Carrier (atom %) | Change in Si Unwashed to Washed (%) |
|---|---|---|---|---|---|---|
| A | 6.1 | 2.7 | 55.7 | 13.4 | 11.5 | 14.2 |
| B | 6.0 | 2.7 | 55.0 | 14.0 | 11.2 | 20.0 |
| C | 3.8 | 0.8 | 78.9 | 11.3 | 10.1 | 10.6 |
| D | 11.2 | 5.8 | 47.9 | 10.4 | 9.7 | 5.9 |
| E | 8.5 | 3.3 | 61.2 | 12.5 | 10.6 | 15.2 | pH Measurement Procedures

Silver solution pH measurements were done using a Metrohm model 744 pH meter, employing a model 6.0220.100 combination electrode and a Pt 100 model 6.1110.100 resistance thermometer for temperature compensation. The meter was calibrated with commercially available buffer solutions before each use. In a typical measurement, a 50 cc aliquot of the doped silver solution to be used for a catalyst impregnation was filtered into a 100 cc glass beaker through a 2 micron filter attached in-line to a plastic syringe. The pH probe was lowered into the magnetically stirred solution, and the reading obtained after 3 minutes was recorded as the equilibrated pH. The probe was cleaned between each measurement with deionized water, and checked for calibration. Special care was taken to prevent accumulation of AgCl solids on the electrode membrane. Such accumulation was removed by soaking the probe in ammonium hydroxide solution, as recommended by the manufacturer.

Example 1

A catalyst pre-cursor was prepared from Carrier A by first subjecting the carrier to carrier washing. Following the wash, approximately 30 grams of washed Carrier A were placed under a 25 mm Hg vacuum for 1 minute at ambient temperature. Approximately 50 grams of the impregnating solution was then introduced to submerse the carrier, and the vacuum was maintained at 25 mm Hg for an additional 3 minutes. The cesium target was 450 ppmw/gram finished catalyst. The vacuum was then released and the excess impregnating solution was removed from the catalyst pre-cursor by centrifugation at 500 rpm for two minutes. The catalyst pre-cursor was then dried while being shaken at 240° C. for 4 minutes in a stream of air flowing at 11.3 m$^3$/hr.

Example 1a (Comparative)

Carrier A was impregnated as described in Example 1; however, the carrier was not subjected to carrier washing. The cesium target was 400 ppmw/gram finished catalyst.

Example 2

Carrier B was subjected to carrier washing and impregnation as described in Example 1. The cesium target was 450 ppmw/gram finished catalyst.

Example 2a (Comparative)

Carrier B was impregnated as described in Example 1; however, the carrier was not subjected to carrier washing. The cesium target was 400 ppmw/gram finished catalyst.

Example 3

Carrier C was subjected to carrier washing and impregnation as described in Example 1. The cesium target was 300 ppmw/gram finished catalyst.

Example 3a (Comparative)

Carrier C was impregnated as described in Example 1; however, the carrier was not subjected to carrier washing. The cesium target was 360 ppmw/gram finished catalyst.

Example 4

Carrier D was subjected to carrier washing and impregnation as described in Example 1. The cesium target was 400 ppmw/gram finished catalyst.

Example 4a (Comparative)

Carrier D was impregnated as described in Example 1; however, the carrier was not subjected to carrier washing. The cesium target was 400 ppmw/gram finished catalyst.

Example 5

Carrier A was subjected to carrier washing and impregnation as described in Example 1. The cesium target was 450 ppmw/gram finished catalyst. In addition, 35% w aqueous tetraethylammonium hydroxide (TEAH) was added to the stock impregnation solution at a target of 117.8 micromoles OH$^-$/cc Ag solution, to lower the hydrogen ion activity to a "measured pH" of 13.2.

Example 6

100 g of Carrier A were immersed in 300 ml of boiling 5% TEAH for 15 min, then immersed six times in 300 ml of boiling de-ionized water for 15 minutes each. The carrier was then removed and dried in a well ventilated oven at 150° C. for 18 hours. The carrier was then impregnated with a cesium target of 400 ppmw/gram finished catalyst. In addition, 35% w TEAH was added to the stock impregnation solution at a target of 117.8 micromoles OH$^-$/cc Ag, to lower the hydrogen ion activity to a "measured pH" of 13.6.

Example 7

Carrier A was subjected to carrier washing and impregnation as described in Example 1. The cesium target was 720 ppmw/gram finished catalyst. In addition, TEAH was dissolved in water and added to the stock solution at a target of 117.8 micromoles OH$^-$/cc Ag, to lower the hydrogen activity to a "measured pH" of 13.2, and NH$_4$ReO$_4$ was dissolved in water and added to the stock solution to provide 1.5 micromoles Re/gram finished catalyst.

Example 8

Carrier A was subjected to carrier washing and impregnation as described in Example 1. The cesium target was 450 ppmw/gram finished catalyst. In addition, LiOH was dissolved in water and added to the stock impregnation solution to lower the hydrogen ion activity to a "measured pH" of 13.2.

Example 8a (Comparative)

Carrier A was impregnated as described in Example 8; however, the carrier was not subjected to carrier washing. The cesium target was 400 ppmw/gram finished catalyst.

Example 9

300 g of Carrier A were immersed in 900 ml of a boiling 0.1 M solution of ammonium acetate for 15 min, then immersed in 300 ml of de-ionized water at 25° C. for 15 minutes, followed by immersion three times in 300 ml of boiling de-ionized water for 15 minutes each. The carrier was then removed and dried in a well ventilated oven at 150° C. for 18 hours. The carrier was then impregnated as described in Example 1. The cesium target was 450 ppmw/gram finished catalyst. In addition, LiOH was dissolved in water and added to the stock impregnation solution to lower the hydrogen ion activity to a "measured pH" of 13.2.

Example 10

The α-alumina source material for Carrier A was washed with de-ionized water at 25° C., then homogenized with the same ingredients used to form Carrier A before extruding, drying, and firing in a muffle furnace. The resulting carrier was designated Carrier E. Carrier E was used to prepare a catalyst in the same manner as described in Example 1. The cesium target was 510 ppmw/gram finished catalyst. In addition, LiOH was dissolved in water and added to the stock impregnation solution to lower the hydrogen ion activity to a "measured pH" of 13.2.

Example 10a (Comparative)

A catalyst was prepared from Carrier E in the same manner as outlined in Example 10; however, the carrier was not subjected to carrier washing. The cesium target was 360 ppmw/gram finished catalyst.

Example 11

100 g of Carrier A were immersed in 300 ml of a boiling 0.1 M solution of barium acetate at 25° C. for 15 min, then immersed in 300 ml of de-ionized water at 25° C. for 15 minutes, followed by immersion three times in 300 ml of boiling de-ionized water for 15 minutes each. The carrier was then removed and dried in a well ventilated oven at 150° C. for 18 hours. The carrier was then impregnated as described in Example 1. The cesium target was 400 ppmw/gram finished catalyst. In addition, LiOH was dissolved in water and added to the stock impregnation solution to lower the hydrogen ion activity to a "measured pH" of 13.2.

Example 12

Carrier A was subjected to carrier washing and impregnation as described in Example 1. The cesium target was 650 ppmw/gram finished catalyst. In addition, LiOH was dissolved in water and added to the stock impregnation solution to lower the hydrogen ion activity to a "measured pH" of 13.2 and $NH_4ReO_4$ was dissolved in water and added to the stock impregnation solution to provide 1.5 micromoles Re/gram finished catalyst.

The catalysts of Examples 1–12 were used to produce ethylene oxide from ethylene and oxygen. 3 to 5 grams of crushed catalyst were loaded into a 6.35 mm inside diameter stainless steel U-shaped tube. The U tube was immersed in a molten metal bath (heat medium) and the ends were connected to a gas flow system. The weight of the catalyst used and the inlet gas flow rate were adjusted to achieve a gas hourly space velocity of 6800 cc of gas per cc of catalyst per hour. The inlet gas pressure was 1450 kPa.

The gas mixture passed through the catalyst bed (in a once-through operation) during the entire test run (including start-up) consisted of 25% ethylene, 7.0% oxygen, 5% carbon dioxide, 63% nitrogen, and 2.0 to 6.0 ppmv ethyl chloride.

The initial reactor (heat medium) temperature was 180° C. The temperature was ramped at a rate of 10° C. per hour from 180° C. to 225° C., and then adjusted so as to achieve a constant ethylene oxide level of 1.5% v in the outlet gas stream. Performance data at this conversion level are usually obtained when the catalyst has been on stream for a total of at least 1–2 days. Due to slight differences in feed gas composition, gas flow rates, and the calibration of analytical instruments used to determine the feed and product gas compositions, the measured selectivity and activity of a given catalyst may vary slightly from one test run to the next.

The initial performance values for selectivity at 1.5% ethylene oxide were measured and are reported in Table IV.

It can be seen that significant improvement in catalyst properties are seen when the carrier is washed before the catalytic metal is deposited on the carrier. Even further improvement is seen when the material used to make the carrier is washed before the carrier is formed.

The hydrogen ion activity of the deposition solution for catalysts in Examples 5–12 was lowered by the addition of a base. It can be seen that lowering the hydrogen ion activity of the deposition solution further improves the catalytic properties. It is also evident that the phenomenon of the pH effect is not restricted to a particular catalyst formulation, as best illustrated in Examples 7 and 12, where a selectivity enhancing dopant, such as rhenium, is added to the impregnating solution.

It will be apparent to one of ordinary skill in the art that many changes and modifications may be made to the invention without departing from its spirit or scope as set forth herein.

I claim:

1. A process for improving the properties of a carrier, said process comprising:

selecting a carrier;

lowering a concentration of one or more ionizable species present on a surface of said carrier, wherein said ionizable species comprise silicates;

depositing a catalytically effective amount of one or more catalytically reactive metals comprising silver on said carrier; and depositing one or more promoters comprising rhenium prior to, coincidentally with, or subsequent to the deposition of said one or more catalytically reactive metals.

2. A process according to claim 1 wherein said concentration of one or more ionizable species is lowered by a means effective in rendering the ionizable species ionic and removing that species, or rendering the ionizable species insoluble, or rendering the ionizable species immobile.

3. A process according to claim 2 wherein said means is selected from washing, ion exchange, volatilization, precipitation, sequestration, and combinations thereof.

TABLE IV

Performance Characteristics of Catalysts Prepared From Unwashed and Washed α-Alumina

| Example | Carrier | pre-Impregnation Condition | Base Addition | Impregnating Solution "measured pH" | Selectivity (%) | Temperature (° C.) |
|---|---|---|---|---|---|---|
| 1 | A | water wash | none | 11.2 | 82.7 | 229 |
| 1a | A | no wash | none | 11.2 | 81.3 | 237 |
| 2 | B | water wash | none | 11.2 | 82.5 | 226 |
| 2a | B | no wash | none | 11.2 | 82.0 | 232 |
| 3 | C | water wash | none | 11.2 | 82.0 | 229 |
| 3a | C | no wash | none | 11.2 | 82.0 | 235 |
| 4 | D | water wash | none | 11.2 | 82.5 | 227 |
| 4a | D | no wash | none | 11.2 | 82.2 | 245 |
| 5 | A | water wash | TEAH | 13.2 | 82.7 | 226 |
| 6 | A | TEAH wash + water wash | TEAH | 13.6 | 82.7 | 222 |
| 7 | A | water wash | TEAH | 13.2 | 89.4 | 245 |
| 8 | A | water wash | LiOH | 13.2 | 82.7 | 226 |
| 8a | A | nb wash | LiOH | 13.2 | 82.0 | 227 |
| 9 | A | ammonium acetate wash | LiOH | 13.2 | 83.1 | 222 |
| 10 | E | raw material wash + carrier body wash | LiOH | 13.2 | 82.7 | 222 |
| 10a | E | raw material wash + no carrier body wash | LiOH | 13.2 | 83.0 | 225 |
| 11 | A | barium acetate wash | LiOH | 13.2 | 82.7 | 226 |
| 12 | A | water wash | LiOH | 13.2 | 86.2 | 232 |

4. A process according to claim 3 wherein said concentration of one or more ionizable species is lowered by washing with an aqueous and/or organic solvent-based solution.

5. A process according to claim 1 further comprising a drying step following said concentration lowering step.

6. A process according to claim 1 wherein said metal deposition is effected by submersing said carrier in an impregnation solution wherein a hydrogen ion activity of said solution is lowered.

7. A process according to claim 6 wherein said hydrogen ion activity is lowered by addition of a base to said impregnation solution.

8. A process according to claim 1 further comprising a drying step following the deposition step.

9. A process according to claim 1 further comprising selecting one or more carrier forming materials and lowering a concentration of one or more ionizable species present in at least one of said one or more materials prior to forming said materials into said carrier.

10. A process for improving the properties of a carrier, said process comprising:
  selecting one or more materials;
  lowering a concentration of one or more ionizable species present in at least one of said one or more materials, wherein said ionizable species comprise silicates;
  forming a carrier comprising said one or more materials;
  lowering a concentration of one or more ionizable species present on a surface of said carrier;
  depositing a catalytically effective amount of one or more catalytically reactive metals comprising silver on said carrier; and
  depositing one or more promoters comprising rhenium prior to, coincidentally with, or subsequent to the deposition of said one or more catalytically reactive metals.

11. A process according to claim 10 wherein said concentration of one or more ionizable species is lowered by a means effective in rendering the ionizable species ionic and removing that species, or rendering the ionizable species insoluble, or rendering the ionizable species immobile.

12. A process according to claim 11 wherein said means is selected from washing, ion exchange, volatilization, precipitation, sequestration, impurity control, and combinations thereof.

13. A process according to claim 12 wherein said concentration of one or more ionizable species is lowered by washing with an aqueous and/or organic solvent-based solution.

14. A process according to claim 10 wherein said meatal deposition is effected by submersing said carrier in an impregnation solution wherein a hydrogen ion activity of said solution is lowered.

15. A process according to claim 14 wherein said hydrogen ion activity is lowered by addition of a base to said impregnation solution.

16. A process for improving the catalytic properties of a catalyst, said process comprising:
  selecting a carrier;
  lowering a concentration of one or more ionizable species on a surface of said carrier by a means effective in solubilizing the ionizable species and removing that species, or rendering the ionizable species insoluble, or rendering the ionizable species immobile, wherein said ionizable species comprise silicates;
  optionally drying said carrier;
  depositing a catalytically effective amount of one or more catalytically reactive metals comprising silver on said carrier, and depositing one or more promoters comprising rhenium prior to, coincidentally with, or subsequent to the deposition of said one or more catalytically reactive metals, thereby forming a catalyst precursor; and
  optionally drying said catalyst precursor.

17. A process according to claim 16 wherein said means is selected from washing, ion exchange, volatilization, precipitation, sequestration, and combinations thereof.

18. A process according to claim 16 wherein said metal deposition is effected by submersing said carrier in an impregnation solution wherein a hydrogen ion activity of said solution is lowered.

19. A process according to claim 18 wherein said hydrogen ion activity is lowered by addition of a base to said impregnation solution.

20. A process according to claim 16 further comprising selecting one or more materials and lowering a concentration of one or more ionizable species present in at least one of said one or more materials prior to forming said materials into said carrier.

21. A process for improving the catalytic properties of a catalyst, said process comprising:
  selecting one or more materials;
  lowering a concentration of one or more ionizable species present in at least one of said one or more materials by a means effective in solubilizing ionizable species and removing that species, or rendering the ionizable species insoluble, or rendering the ionizable species immobile, wherein said ionizable species comprise silicates;
  forming a carrier comprising said one or more materials;
  optionally lowering a concentration of one or more ionizable species on a surface of said carrier by a means effective in solubilizing and removing said ionizable species or rendering said ionizable species insoluble;
  optionally drying said carrier;
  depositing a catalytically effective amount of one or more catalytically reactive metals comprising silver on said carrier, and depositing one or more promoters comprising rhenium prior to, coincidentally with, or subsequent to the deposition of said one or more catalytically reactive metals, thereby forming a catalyst precursor; and
  optionally drying said catalyst precursor.

22. A process according to claim 21 wherein said means is selected from washing, ion exchange, volatilization, precipitation, sequestration, and combinations thereof.

23. A process according to claim 21 wherein said metal deposition is effected by submersing said carrier in an impregnation solution wherein a hydrogen ion activity of said solution is lowered.

24. A process according to claim 23 wherein said hydrogen ion activity is lowered by addition of a base to said impregnation solution.

25. A process for preparing a catalyst suitable for the vapor phase production of epoxides, said process comprising:
  selecting a carrier;
  lowering a concentration of one or more ionizable species present on a surface of said carrier, wherein said ionizable species comprise silicates;
  optionally drying said carrier;

depositing a catalytically effective amount of one or more catalytically reactive metals comprising silver on said carrier, and depositing one or more promoters comprising rhenium prior to, coincidentally with, or subsequent to the deposition of said one or more catalytically reactive metals.

26. A process according to claim 25 wherein said carrier is an inorganic carrier.

27. A process according to claim 25 wherein said concentration of one or more ionizable species is lowered by a means effective in rendering the ionizable species ionic and removing that species, or rendering the ionizable species insoluble, or rendering the ionizable species immobile.

28. A process according to claim 27 wherein said means is selected from washing, ion exchange, volatilization, precipitation, sequestration, and combinations thereof.

29. A process according to claim 28 wherein said concentration of said one or more ionizable species is lowered by washing with an aqueous and/or organic solvent-based solution.

30. A process according to claim 29 wherein said aqueous and/or organic solvent-based solution is selected from water, tetraethylammonium hydroxide, ammonium acetate, lithium carbonate, barium acetate, strontium acetate, crown ether, methanol, ethanol, dimethylformamide, and mixtures thereof.

31. A process according to claim 25 further comprising depositing one or more promoters, other than rhenium, selected from sulfur, phosphorus, boron, fluorine, Group IA through Group VIII metals, rare earth metals, and combinations thereof.

32. A process according to claim 31 wherein said Group IA metal is selected from potassium, rubidium, cesium, lithium, sodium, and combinations thereof.

33. A process according to claim 31 wherein Group IIA metal is selected from magnesium, calcium, strontium, barium, and combinations thereof.

34. A process according to claim 31 wherein said Group VIII metal is selected from cobalt, iron, nickel, ruthenium, rhodium, palladium, and combinations thereof.

35. A process according to claim 31 wherein said rare earth metal is selected from lanthanum, cerium, neodymium, samarium, gadolinium, dysprosium, erbium, ytterbium, and combinations thereof.

36. A process according to claim 31 wherein said carrier is an alumina-based carrier.

37. A process according to claim 36 wherein said silver deposition is effected by submersing said carrier in an impregnation solution wherein a hydrogen ion activity of said solution is lowered.

38. A process according to claim 37 wherein said hydrogen ion activity is lowered by addition of a base to said impregnation solution.

39. A process according to claim 25 further comprising selecting one or more materials and lowering a concentration of one or more ionizable species present in at least one of said one or more materials prior to forming said materials into said carrier.

* * * * *